United States Patent [19]

Liss et al.

[11] Patent Number: 5,789,491
[45] Date of Patent: Aug. 4, 1998

[54] FLUORINATED MELT ADDITIVES FOR THERMOPLASTIC POLYMERS

[75] Inventors: Theodor Arthur Liss, Wilmington; Kimberly Gheysen Raiford; Edward James Greenwood, both of Hockessin, all of Del.

[73] Assignee: E. I. du Pont de Nemours and Company, Wilmington, Del.

[21] Appl. No.: 878,803

[22] Filed: Jun. 19, 1997

Related U.S. Application Data

[62] Division of Ser. No. 579,045, Dec. 21, 1995, Pat. No. 5,681,963.
[51] Int. Cl.$^6$ ..................................................... C08F 283/04
[52] U.S. Cl. .......................... 525/420; 525/437; 548/455; 548/481; 548/433; 548/545; 548/546; 548/547; 428/473.5; 428/474.4; 428/480
[58] Field of Search .................. 525/420, 437; 548/455, 481, 433, 545, 546, 547; 428/473.5, 474.4, 480

*Primary Examiner*—Helen L. Pezzuto

[57] ABSTRACT

Fluorinated imides useful for imparting repellency of low surface tension fluids to thermoplastic polymers of formulae

A.

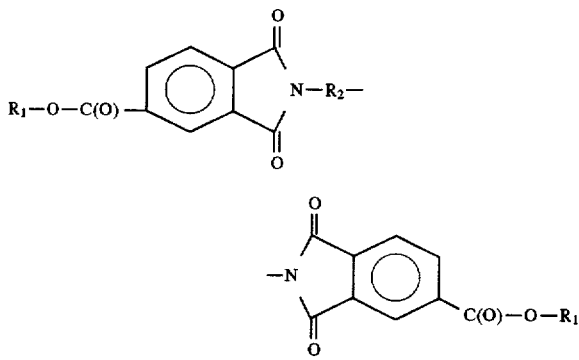

B.

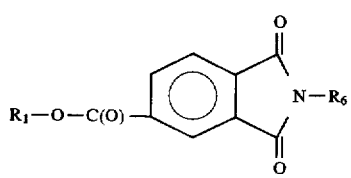

—continued

C.

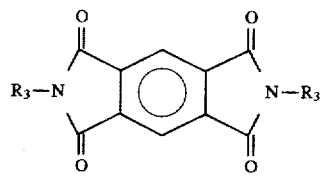

D.

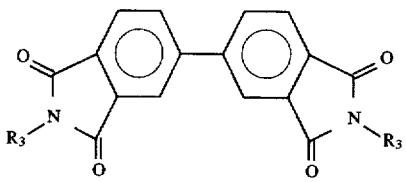

E.

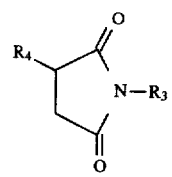

wherein $R_1$ is $F(CF_2)_x$—$(CH_2)_m$, or $F(CF_2)_xSO_2N(R_5)(CH_2)p$ wherein x is from about 4 to about 20, m is from about 2 to about 6, p is from 1 to about 12, and $R_5$ is an alkyl radical of from 1 to about 4 carbons;

$R_2$ is a linear, branched or cyclic alkylene or poly(oxyalkylene) hydrocarbon group having from about 2 to about 15 carbons;

$R_3$ is selected from the group consisting of $F(CF_2)_x$—$(CH_2)_m$, $F(CF_2)_x$—$(CH_2)_m$—$OC(O)$—$(CH_2)_n$, and $F(CF_2)_xSO_2N(R_5)(CH_2)_pOC(O)(CH_2)_n$ wherein x is from about 4 to about 20, m is from about 2 to about 6, n is about 2 to about 12, p is from 1 to about 12, and $R_5$ is an alkyl radical of from 1 to about 4 carbons;

$R_4$ is an alkyl or alkenyl group of from about 4 to about 20 carbons, and $R_6$ is a linear or branched alkyl having from about 4 to about 20 carbons.

7 Claims, No Drawings

FLUORINATED MELT ADDITIVES FOR THERMOPLASTIC POLYMERS

This is a division of application Ser. No. 08/579,045, filed Dec. 21, 1995, now U.S. Pat. No. 5,681,963.

FIELD OF THE INVENTION

This invention relates to certain novel fluorinated imides and to a process for imparting superior repellency of low surface tension fluids to thermoplastic polymers, in particular fibers, fabrics, nonwovens, films and molded articles, by the addition of these imides to the polymer.

BACKGROUND OF THE INVENTION

Thermoplastic polymer fibers are frequently treated with fluorochemical compounds in order to affect the surface characteristics of the fiber, for example to improve water repellency or to impart stain or dry soil resistance. Most frequently, fluorochemical dispersions are applied topically to the fabrics made from these fibers by spraying, padding or foaming, followed by a drying step to remove water.

For example, a method is known for obtaining dry soil resistance and nonflame propagating characteristics in a textile fiber by applying topically aqueous dispersions of a variety of fluorinated esters derived from perfluoroalkyl aliphatic alcohols of the formula $C_nF_{2n+1}(CH_2)_mOH$ where n is from about 3 to 14 and m is 1–3, together with mono- or polycarboxylic acids which contain from 3 to 30 carbons and can contain other substituents. The fluorinated esters include, among others, a perfluoroalkylstearate corresponding to "ZONYL" FTS.

It is well recognized that the process of manufacturing thermoplastic polymeric fibers could be simplified and significant capital investment could be eliminated if the topical application were replaced by incorporating a fluorochemical additive into the polymer melt prior to the extrusion of the fiber. The difficulty has been in finding suitably stable and effective fluorochemical additives.

Thermoplastic polymers include, among others, polyolefins, polyesters, polyamides and polyacrylates. Polyolefins and in particular polypropylene are frequently used for disposable nonwoven protective garments, particularly in the medical/surgical field, in part because of polyolefin's inherent water-repellency. However, polyolefins are not inherently good repellents for other lower surface tension fluids frequently encountered in the medical field such as blood and isopropyl alcohol. To get around this deficiency, fluorochemical dispersions are applied topically to these fabrics.

The requirements of an additive suitable for incorporating into a polyolefin melt include, besides the ability to repel low surface tension fluids at a low concentration of the additive, a satisfactory thermal stability and volatility to withstand processing conditions. Preferably the compound will migrate to the surface of the fiber so as to minimize the amount of additive needed for adequate repellency. While this migration can often be enhanced by post-extrusion heating of the fiber, it is more preferable for the migration to occur without the need for this heating step. This requirement for mobility in the polymeric fiber in turn tends to limit the size of the fluorochemical molecule, and effectively eliminates from consideration high molecular weight polymeric fluorochemical additives.

The general concept of incorporating fluorochemical additives into a polyolefin fiber melt is known, but the difficulty in finding suitable effective additives has limited the application of this concept. Many of the past efforts to evaluate such fluorochemical additives have been aimed at improving other properties of the polyolefin, and do not teach methods of improving its repellency to low surface tension fluids.

Nonwoven composite structures are known consisting in part of two or more melt-extruded nonwoven layers, at least one of which includes an additive which imparts to the surface at least one characteristic different than the surface characteristics of the polymer alone as a result of preferential migration of the additive to the surface without the need for post-formation treatment of any kind. Examples of the additive-including layer include polypropylene polymer modified by commercially available fluorochemical additives, including "ZONYL" FTS above.

U.S. Pat. No. 5,178,931 and U.S. Pat. No. 5,178,932 disclose specific nonwoven laminiferous and composite structures respectively, consisting in part of three melt-extruded nonwoven layers, the second of which includes an additive which imparts alcohol repellency as a result of preferential migration of the additive to the surface without the need for post-formation treatment of any kind, and where at least one of the first and third layers has been treated by topical application of an agent to change its characteristics in some way. Examples of the additive included in the second layer include commercially available fluorochemicals, including "ZONYL" FTS.

Soil resistant polymeric compositions are known which are prepared by melt extrusion with a nonpolymeric fluorochemical dispersed throughout the polymer. The polymers used include polypropylene, polyethylene, polyamide and polyester, and the fluorochemical used is a perfluoroalkylstearate, in particular "ZONYL" FTS.

In summary, while the prior art discloses numerous examples of polyolefin fibers containing a fluorochemical additive incorporated at the melt stage to alter the surface characteristics of the extruded fiber, much of the previous work was aimed at soiling and staining resistance or water repellency. Those references which disclose imparting alcohol repellency to polyolefin fabrics employ "ZONYL" FTS. A need exists to achieve superior repellency for low surface tension fluids and superior product efficiency. The fluorinated compounds of the present invention meet this need.

SUMMARY OF THE INVENTION

The present invention comprises a compound of formula A:

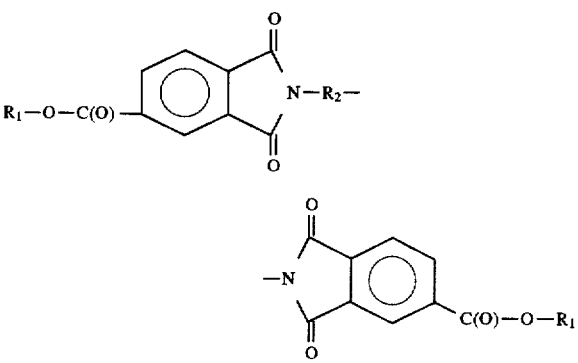

wherein $R_1$ is $F(CF_2)_x$—$(CH_2)_m$ or $F(CF_2)_xSO_2N(R_5)(CH_2)_p$
wherein x is from 1 about 4 to about 20, m is from about 2 to about 6, p is from 1 to about 12, and $R_5$ is an alkyl radical of from 1 to about 4 carbons and $R_2$ is a linear, branched or cyclic alkylene or poly (oxyalkylene) hydrocarbon group having from about 2 to about 15 carbons.

The present invention further comprises a compound of formula B:

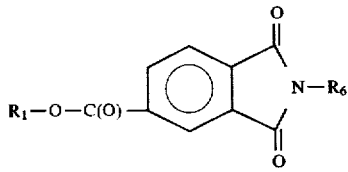

wherein $R_1$ is as defined above, and $R_6$ is a linear or branched alkyl having from about 4 to about 20 carbons.

The present invention further comprises a compound of formula C:

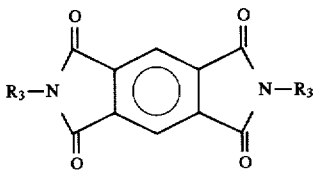

wherein $R_3$ is selected from the group consisting of $F(CF_2)_x$—$(CH_2)_m$, $F(CF_2)_x$—$(CH_2)_m$—$OC(O)$—$(CH_2)_n$, and $F(CF_2)_xSO_2N(R_5)(CH_2)_pOC(O)(CH_2)_n$ wherein x is from about 4 to about 20, m is from about 2 to about 6, n is about 2 to about 12, p is from 1 to about 12, and $R_5$ is an alkyl radical of from 1 to about 4 carbons.

The present invention further comprises a compound of formula D:

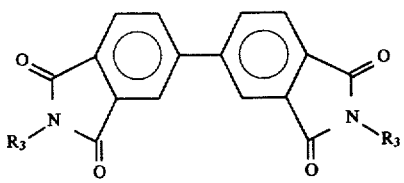

wherein $R_3$ is as defined above, for formula C.

The present invention further comprises a compound of formula E:

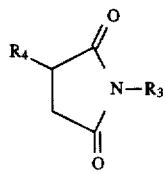

wherein $R_3$ is as defined above for formula C and $R_4$ is an alkyl or alkenyl group of from about 4 to about 20 carbons.

The present invention further comprises a composition comprising at least one thermoplastic polymer and at least one compound selected from the group consisting of formula A, formula B, formula C, formula D and formula E as defined above.

The present invention further comprises an extruded filament, fiber, film, molded article, and nonwoven web or fabric, each comprising at least one thermoplastic polymer and at least one compound selected from the group consisting of formula A, formula B, formula C, formula D and formula E as defined above.

The present invention further comprises a process for imparting superior repellency of low surface tension fluids to thermoplastic polymer articles of manufacture comprising forming a mixture prior to article formation of a polymer and an effective amount of a compound of formula A, B, C, D or E, or mixtures thereof as defined above, and melt extruding the mixture. This process is particularly suitable for imparting repellency of low surface tension fluids to polyolefin articles, and may be used either with or without post-extrusion heating of the article to promote movement of the additive to the article surface. "Articles" is used herein to include filaments, fibers, nonwoven webs or fabrics, films, and molded articles.

DETAILED DESCRIPTION OF THE INVENTION

Superior repellency to low surface tension fluids can be imparted to thermoplastic polymer articles of manufacture or substrates, such as filaments, fibers, nonwoven webs or fabrics, films, or molded articles, by forming a mixture by the addition of certain monomeric fluorinated imide compounds to a polymer prior to article formation, and melt extruding the mixture.

The term "low surface tension fluids" is used herein to mean fluids having a surface tension of less than 50 dynes/cm($50 \times 10^{-7}$ newton meter). Examples of such fluids include alcohols, oils and certain body fluids such as blood.

The compounds of the present invention comprise the following groups of fluorinated imides compounds: Formula A.

Formula A.

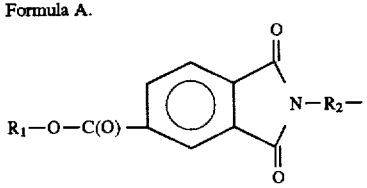

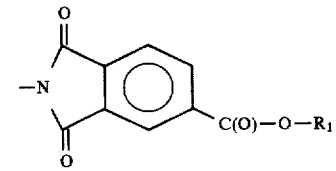

Formula B.

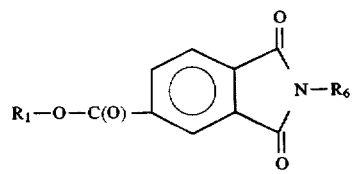

Formula C.

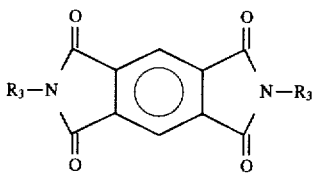

Formula D.

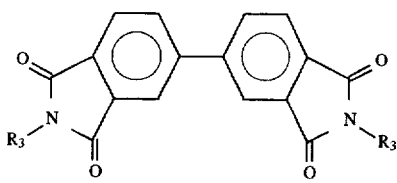

Formula E.

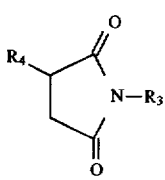

wherein

- $R_1$ is $F(CF_2)_x$—$(CH_2)_m$, or $F(CF_2)_xSO_2N(R_5)(CH_2)_p$ wherein x is from about 4 to about 20, m is from about 2 to about 6, p is from 1 to about 12, and $R_5$ is an alkyl radical of from 1 to about 4 carbons;
- $R_2$ is a linear, branched or cyclic alkylene or poly (oxyalkylene) hydrocarbon group having from about 2 to about 15 carbons;
- $R_3$ is selected from the group consisting of $F(CF_2)_x$—$(CH_2)_m$, $F(CF_2)_x$—$(CH_2)_m$—$OC(O)$—$(CH_2)_n$, and $F(CF_2)_xSO_2N(R_5)(CH_2)_pOC(O)(CH_2)_n$ wherein x is from about 4 to about 20, m is from about 2 to about 6, n is about 2 to about 12, p is from 1 to about 12, and $R_5$ is an alkyl radical of from 1 to about 4 carbons, and
- $R_4$ is an alkyl or alkenyl group of from about 4 to about 20 carbons, and
- $R_6$ is a linear or branched alkyl having from about 4 to about 20 carbons.

In the compounds of this invention, the value of x in the definition of $R_1$ for formulae A and B and in the definition of $R_3$ for formulae C, D and E, which represents the length of the fluorinated carbon chain moiety, has preferably an average value of from 7 to about 10. Especially preferred is a composition wherein $R_1$ for formula A and B is $F(CF_2)_x$—$(CH_2)_m$ and $R_3$ for formula C, D and E is $F(CF_2)_x$—$(CH_2)_m$—$OC(O)$—$(CH_2)_m$ and the chain length distributions and their weight percent are as follows:

x=6 or less 0–10% by weight
x=8 45–75% by weight
x=10 20–40% by weight
x=12 1–20% by weight
x=14 or greater 0–5% by weight.

This composition range, when m=2, is hereinafter referred to as Telomer BN.

There are various methods by which the above compounds can be prepared, and the inventive process is not limited to a particular method of preparation. Compounds in these groups can be readily made by those skilled in the art by following similar processes to those described below.

The compounds of formula A illustrated by Examples 1–13 hereinafter, are made using a 3-step sequence. First, a diamine is reacted with two equivalents of trimellitic anhydride in refluxing acetic acid. The products are isolated at room temperature by vacuum filtration. Next, the trimellitic anhydride/diamine adducts are converted to the intermediate acid chloride with thionyl chloride and subsequently reacted in situ with Telomer BN alcohol to form the fluorinated ester.

The compounds of formula B, illustrated by Examples 14–15 hereinafter, are made using a 2-step sequence. First a monoamine is reacted with one equivalent of trimellitic anhydride in refluxing acetic acid. After isolation, the trimellitic anhydride/monoamine adducts are reacted neat with Telomer BN alcohol at about 140° C. to form the fluorinated ester.

The compounds of formula C and formula D, illustrated by Examples 16–21 hereinafter, are prepared by the reactions of one equivalent of either pyromellitic dianhydride (PMDA) or biphenyltetracarboxylic acid dianhydride (BPDA) with two equivalents of an amine in refluxing acetic acid. Bisimides are produced by condensing 3-perfluoroalkylpropyl amine with PMDA and BPDA. Alternatively compounds of formula C and formula D are made by first reacting an amino acid with either PMDA or BPDA. In a second step, the dianhydride/amino acid adducts are converted to the corresponding acid chlorides with thionyl chloride and subsequently reacted in situ with Telomer BN alcohol to form the fluorinated esters.

The compounds of formula E, illustrated by Examples 22–26 hereinafter, are prepared by two step reactions in which alkyl or alkenyl succinic anhydrides are reacted first with an amino acid in refluxing acetic acid. The isolated adducts are converted to the esters by direct esterification with Telomer BN alcohol at about 140° C.

The compounds of this invention are mixed with thermoplastic polymers by adding them to granular, pelletized, powdered, or other appropriate forms of the polymers and rolling, agitating or compounding the mixture to achieve a uniform mixture, followed by melt extruding the mixture. Alternatively, the compounds of this invention are added to a polymer melt to form a mixture which is then melt extruded. The thermoplastic polymer is a polyolefin, polyester, polyamide, or polyacrylate. Preferably the thermoplastic polymer is a polyolefin, mixture of polyolefins, a polyolefin copolymer, mixture of polyolefin copolymers, or a mixture of at least one polyolefin and at least one polyolefin copolymer. The thermoplastic polymer is more preferably a polyolefin or copolymer wherein the polymer unit or copolymer unit is ethylene, propylene, or butylene or mixtures thereof. Thus the polyolefin is polyethylene, polypropylene, polybutylene or a blend thereof or copolymers thereof.

The amount of the fluorinated compound added to the thermplastic polymer is preferably between 0.1 and about 5% by weight of the polymer. Amounts above this range can be used but are unnecessarily expensive in relation to the benefit received. Below this range the benefit is too small for practical use. The blend is then melted and extruded into filaments, fibers, nonwoven fabrics or webs, films, or molded articles using known methods. The fluorine content of the filament, fiber, nonwoven fabrics or webs, film or molded article is from about 200 µg/g to about 25,000 µg/g.

Extrusion is used to form various types of nonwovens. In particular, extrusion is used to form a melt blown nonwoven web of continuous and randomly deposited microfibers having an average diameter of approximately 0.1 to 10 microns, preferably in the range of about 3 to 5 microns. The melt extrusion is carried out through a die at a resin flow rate of at least 0.1 to 5 grams per minute per hole, with the microfibers being randomly deposited on a moving support to form the web.

In the above melt blowing process, polymer and a compound of the present invention are fed into an extruder where it is melted and passed through a die containing a row of tiny orifices. As the polymer emerges from the die, it is contacted by two converging, high-velocity hot air streams, which attenuate the polymer into a blast of fine, discontinuous fibers of 0.1 to about 10 microns in diameter. The useful polymer throughputs or flow rates range from 0.1 to 5 grams per minute per hole. Typical gas flow rates range from 2.5 to 100 pounds per square inch ($1.72 \times 10^5$ to $6.89 \times 10^5$ Pa) per minute of gas outlet area. The air temperature ranges from about 400° F.(204° C.) to 750° F. (399° C.). Cooling air then quenches the fibers, and they are deposited as a random, entangled web on a moving screen which is placed 6 to 12 inches (15.2 to 30.5 cm) in front of the blast of fibers.

Melt blowing processes are described in further detail in articles by V. A. Wente, "Superfine Thermoplastic Fibers", Industrial and Engineering Chemistry, Vol. 48(8), pp 1342–1346 (1956); and by R. R. Buntin and D. T. Lohkamp, "Melt Blowing—A One-step Web Process for New Nonwoven Products", Journal of the Technical Association of the Pulp and Paper Industry, Vol. 56(4), pp 74–77 (1973); as well as in U.S. Pat. No. 3,972,759 to R. R. Buntin. The disclosures of these documents are hereby incorporated by reference.

The unique properties of a melt blown nonwoven web comprised of a random array of fine, entangled fibers include very large surface areas, very small pore sizes, moderate strength and light weight fabric structure. These properties make the nonwoven webs particularly suitable for such applications as medical fabrics where barrier properties as well as breathability and drape are important. The method used for blending and melt extrusion of test materials is described further in the examples below.

Extrusion is also used to form polymeric films. In film applications, a film-forming polymer and a compound of the present invention are simultaneously melted and mixed as they are conveyed through the extruder by a rotating screw or screws and then forced out through a slot or flat die, for example, where the film is quenched by a variety of techniques known to those skilled in the art. The films optionally are oriented prior to quenching by drawing or stretching the film at elevated temperatures.

Molded articles are produced by pressing or injecting molten polymer containing a compound of the present invention from a melt extruder as described above into a mold where the polymer solidifies. Typical melt forming techniques include injection molding, blow molding, compression molding and extrusion, and are well known to those skilled in the art. The molded article is then ejected from the mold and optionally, heat-treated to effect migration of the polymer additives to the surface of the article.

An optional heating or annealing step can be conducted but is not required. The polymer melt or extruded fiber, filament, nonwoven web, film, or molded article is heated to a temperature of from about 25° C. to about 150° C. The heating in some cases may improve the effectiveness of the fluorochemical additive in imparting alcohol repellency.

The compounds and compositions of the present invention are useful in various filaments, fibers, nonwoven webs or fabrics, films and molded articles. Examples include fibers for use in fabrics and carpets, nonwoven fabrics used in protective garments used in the medical/surgical field, and molded plastic articles of many types. The processes of the present invention are useful for imparting repellency of low surface tension fluids in various thermoplastic polymer articles such as filaments, fibers, nonwoven webs or fabrics, films and molded articles.

EXAMPLE 1

Step 1

Into a 5-liter flask equipped with a condenser and containing 2250 mL of glacial acetic acid was added over about one hour 111 g (1.48 mole) 1,2-diaminopropane (Aldrich, 99%), followed by 616 g (3.06 mole) trimellitic anhydride (Amoco, 95.5% minimum) and 375 mL acetic acid. After heating at reflux for 14 hours, the reaction mass was filtered off at room temperature. The cake was washed with acetic acid, and then with water until free of acid. After drying at 115° C. in a vacuum oven, a white solid was obtained yielding 591 g (93.4%); m.p. 323° C. (DSC).

Steps 2 and 3

Into a dry 5-liter four-necked flask equipped with a condenser containing a nitrogen inlet and connected to a caustic scrubber through a drying tube were added, in turn, 254 g (0.6 mole) trimellitic anhydride/1,2-diaminopropane adduct (step 1), 2500 mL dichloroethane, 1.0 g (0.004 mole) benzyltriethylammonium chloride and 87 mL (1.19 mole) thionyl chloride. The mixture became clear after heating at reflux for 28 hours. To the clear yellow solution at 60° C. was added 660 g (1.25 mole) dry Telomer EN alcohol. After the reaction mass was cooled to room temperature, 140 g (1.38 mole) triethylamine was added dropwise over about one hour. The temperature was raised to 70° C. and held for one hour. Some foam formation due to the thickness of the reaction mass was observed. The solid product was filtered off at room temperature, washed with isopropyl alcohol, slurried in isopropyl alcohol at 60° C., filtered, washed with isopropyl alcohol and finally water. After drying in a 50° C. vacuum oven, a white solid was obtained yielding 636 g (74%); m.p. 148° C. (DSC). The product was a compound of formula A having $R_2$ equal to $$(\underset{\underset{CH_3}{|}}{CH}-CH_2)_3$$

and $R_1$ equal to Telomer EN.

EXAMPLES 2–13

Examples 2–13 were prepared using the procedure of Example 1 and the appropriate amine as required by the $R_2$ listed below. The compounds obtained were of formula A with definitions of $R_2$ and melting points as listed below and $R_1$ equal to Telomer EN.

|  |  | MP (°C. by DSC) |
|---|---|---|
| Example 2 | $R_2 = (CH_2)_3$ | 141 |
| Example 3 | $R_2 = (CH_2)_4$ | 151 |
| Example 4 | $R_2 = (CH_2)_6$ | 135 |
| Example 5 | $R_2 = (CH_2)_8$ | 126 |
| Example 6 | $R_2 = (CH_2)_{12}$ | 123 |
| Example 7 | $R_2 = (CH_2-\underset{\underset{CH_3}{|}}{CH}-CH_2CH_2CH_2)$ | 131 |

| | | MP (°C. by DSC) |
|---|---|---|
| Example 8 | $R_2 = (CH-CH_2CH_2)$ with $CH_2CH_3$ | 103 |
| Example 9 | $R_2 = C_6H_{10}-CH_2-C_6H_{10}$, $C_6H_{10}$ = cyclohexylene | 172 |
| Example 10 | $R_2$ = isophorone | 115 |
| Example 11 | $R_2 = (CH_2-C(CH_3)_2-CH_2)$ | 164 |
| Example 12 | $R_2 = (CH_2)_3-O-(CH_2)_4-O-(CH_2)_3$ | 102 |
| Example 13 | $R_2$ = 1,3-cyclohexan-diyl | 112 |

EXAMPLE 14

Step 1

A trimellitic anhydride/dodecylamine adduct was prepared using the procedure of Example 1 Step 1, except that one equivalent of trimellitic anhydride was reacted with dodecylamine.

Step 2

Into a 250 mL 4-neck flask equipped with a mechanical stirrer, temperature control device, Dean-Stark trap with a condenser and nitrogen gas inlet and outlet tubes were added 50.0 g (0.125 mole) trimellitic anhydride/dodecylamine adduct (Step 1) and 74.0 g (0.14 mole) Telomer BN alcohol. The mixture was heated until melted, then 0.4 g (0.0034 mole) phosphorous acid and 0.16 g (0.0026 mole) boric acid were added. The mixture was heated to 140° C. and held for approximately 5 days until all alcohol and acid had reacted as determined by gas chromatography and C-13 NMR analyses, respectively. A compound of formula B was obtained wherein $R_6$ was $(CH_2)_{11}$—$CH_3$ and $R_1$ was Telomer BN. Isolated yield: 96.3 g (84.5%); %F found: 38.0; %F calc'd: 41.8; m.p. 41.3° C. (DSC).

EXAMPLE 15

Example 15 was prepared using the procedure of Example 14, except that the trimellitic anhydride was reacted with octadecylamine. A compound of formula B was obtained wherein $R_6$ was $(CH_2)_{17}$—$CH_3$ and $R_1$ was Telomer BN having a m.p. of 62.1° C. by DSC.

EXAMPLE 16

In a 250 mL flask equipped with a condenser, a mixture of 5.45 g (0.025 mole) pyromellitic dianhydride (PMDA) and 29.0 g (0.06 mole) 3-(perfluoroalkyl)-propylamine in 150 mL of glacial acetic acid was heated at reflux overnight. The solid which separated at room temperature was filtered off, washed with acetic acid followed by water until free of acid. After drying in a vacuum oven at 100° C., a white solid was obtained yielding 29.1 g (98.7%); m.p. 209°–214° C. (DSC). The compound obtained was that of formula C wherein $R_3$ was $(CH_2)_3$—$(CF_2)_x$ F wherein x=6–18 as defined for Telomer BN.

EXAMPLE 17

Step 1

Into a 1-liter flask equipped with a condenser was added 500 mL of glacial acetic acid, 43.6 g (0.20 mole) pyromellitic anhydride and 56.2 g (0.42 mole) 6-aminocaproic acid (98%). After heating at reflux for 14 hours, the reaction mass was filtered off at room temperature. The cake was washed with acetic acid, and then with water until free of acid. After drying at 100° C. in a vacuum oven, a white solid was obtained yielding 81.4 g (91.60%); m.p. 250° C. (DSC).

Step 2

Into a dry 1-liter four-necked flask equipped with a condenser containing a nitrogen inlet and connected to a caustic scrubber through a drying tube were added, in turn, 13.3 g (0.03 mole) pyromellitic anhydride/6-aminocaproic acid adduct (Step 1), 300 mL dichloroethane, 0.06 g (0.00026 mole) benzyltriethylammonium chloride and 4.3 mL (0.059 mole) thionyl chloride. The mixture became clear after heating at reflux for 3 hours. To the clear solution at 70° C. was added 33.0 g (0.06 mole) dry Telomer BN alcohol. After the reaction mass was cooled to 50° C., 6.7 g (1.38 mole) triethylamine was added dropwise. The temperature was raised to 65° C. and held for one and a half hours. The solid product was filtered off at room temperature, washed with 1,2-dichloroethane and isopropyl alcohol, slurried in isopropyl alcohol at 60° C., filtered, washed with isopropyl alcohol and finally water. After drying in a 100° C. vacuum oven, a white solid was obtained yielding 32.3 g (73.6%); %F found: 44.6; %F calc'd: 49.3w m.p. 172° C. (DSC). The compound obained was that of formula C wherein $R_3$ was $(CH_2)_5$—$C(O)$—$O$—$(CH_2)_2$—$(CF_2)_xF$ wherein x=6–18 as defined for Telomer BN.

EXAMPLES 18–21

Examples 18 and 19 of formula C were prepared from reaction of pyromellitic dianhydride with 4-aminobutyric acid and beta-alanine, respectively, to yield intermediates which were then reacted with Telomer BN alcohol. The procedure of Example 17 was employed with the above-named starting materials. Example 20, a compound of formula D, was prepared using the procedure of Example 16 above using reactants 3,4,3',4'-biphenyltetracarboxylic dianhydride (BPDA) and 3-(perfluoroalkyl) propyl amine. Example 21, a compound of formula D, was prepared using the procedure of Example 17 by reacting BPDA with 6-aminocaproic acid to yield an intermediate which was then reacted with Telomer BN alcohol. The compounds obtained had $R_3$ as listed below. In all cases, x represented the Telomer BN distribution.

| | m.p. (°C. by DSC) |
|---|---|
| Example 18 $R_3 = (CH_2)_3$—$C(O)$—$O$—$(CH_2)_2$—$(CF_2)_xF$ | 166 |
| Example 19 $R_3 = (CH_2)_2$—$C(O)$—$O$—$(CH_2)_2$—$(CF_2)_xF$ | 182 |
| Example 20 $R_3 = (CH_2)_3$—$(CF_2)_xF$ | 161 |
| Example 21 $R_3 = (CH_2)_5$—$C(O)$—$O$—$(CH_2)_2$—$(CF_2)_xF$ | 171 |

EXAMPLE 22

Step 1

In a 1 L flask equipped with a condenser, a mixture of 46.8 g (0.35 mole) 6-aminocaproic acid and 96.1 g (0.35 mole) 2-dodecen-1-ylsuccinic anhydride (97%) in 500 mL of glacial acetic acid was heated at reflux overnight. After diluting the reaction mixture with cold water and cooling in an ice bath the solid which separated was filtered off, washed with acetic acid followed by water until free of acid. After drying in a vacuum oven at 50° C., a white solid was obtained yielding 120.0 g (90.4%).

Step 2

Into a 250 mL 4-neck flask equipped with a mechanical stirrer, temperature control device, Dean-Stark trap with a condenser and nitrogen gas inlet and outlet tubes were added 45.5 g (0.12 mole) dodecenylsuccinic anhydride/caproic acid adduct (Step 1) and 65.8 g (0.125 mole) Telomer EN alcohol. The mixture was heated until melted, then 0.2 g (0.0017 mole) phosphorous acid and 0.08 g (0.0013 mole) boric acid were added. The mixture was heated to 140° C. and held for approximately 2 days until all alcohol and acid had reacted as determined by gas chromatography and C-13 NMR analyses, respectively. A compound of formula E was obtained having $R_4$=$CH_2CH=CH$—$(CH_2)_9H$ and $R_3$= $(CH_2)_5$—$C(O)$—$O$—$(CF_2)_xF$ wherein x was the Telomer EN distribution. Isolated yield: 98.4 g (92.4%); % fluorine found: 41.0; % fluorine calc'd: 41.0; m.p. 40.4° C. (DSC)

EXAMPLES 23–26

Examples 23–26 were prepared using the procedure of Example 22 above and the appropriate reactants as follows: for Example 23—2-dodecen-1-ylsuccinic anhydride and beta-alanine, for Example 24—2-octadecen-1-ylsuccinic anhydride and 6-aminocaproic acid, for Example 25—2-octadecen-1-ylsuccinic anhydride and beta-alanine and for Example 26—2-octadecylsuccinic anhydride and 6-aminocaproic acid. Compounds of formula E were obtained having $R_4$ and $R_3$ as defined below. In all cases, x represented the Telomer BN distribution.

| Example | $R_4$ | $R_3$ | m.p. (°C. by DSC) |
|---|---|---|---|
| 23 | $CH_2CH=CH$—$(CH_2)_9H$, | $(CH_2)_2$—$C(O)$—$O$—$(CF_2)_xF$ | 42.9 |
| 24 | $CH_2CH=CH$—$(CH_2)_{15}H$, | $(CH_2)_5$—$C(O)$—$O$—$(CF_2)_xF$ | 65.3 |
| 25 | $CH_2CH=CH$—$(CH_2)_{15}H$, | $(CH_2)_2$—$C(O)$—$O$—$(CF_2)_xF$ | 67.8 |
| 26 | $(CH_2)_{18}H$, | $(CH_2)_5$—$C(O)$—$O$—$(CF_2)_xF$ | 83.0 |

EXAMPLE 27

Step 1. Preparation of the Polymer Blend

Uniform mixtures of the fluorochemical additives produced in Examples 1 through 26 together with a polyolefin were prepared by combining them and rolling the mixture for 24 hours. The polyolefin used was Escorene PD3545G or PD3746G (Exxon Chemical Company, P.O. Box 3272, Houston, Tex. 77001) polypropylene resin having a melt flow rate of approximately 800 and 1000 respectively. A comparative example using "ZONYL" FTS, a compound described in prior art, was prepared in a similar manner.

In particular, for the compound of Example 1, a uniform mixture of 10.7 g of finely ground compound of Example 1 and 1889 g Escorene PD3746G (Exxon Chemical Company, P.O. Box 3271, Houston, Tex. 77001) polypropylene having a melt flow rate of approximately 1000 was prepared by rolling the mixture for 24 hours. The fluorine concentration in the mixture was calculated to be 3300 ppm fluorine. Actual fluorine concentration in the nonwoven web was 2660 ppm fluorine.

Step 2. Melt Blown Web Formation

Melt blown nonwoven webs were prepared from the above mixtures using a 6-inch (15 cm) melt blowing pilot unit at a polymer feed rate of about 0.4 gram/minute/hole. The polymer blends were fed into the extruder having three barrel zones at temperatures ranging from 175° to 250° C. The temperature of the die ranged from 200° to 260° C. and the air temperature at the die varied from 200° to 270° C. The die tip gap was 0.060 inches (0.15 cm) and the primary air pressure was 2.6 psi (17.9×10³ Pa). The webs were formed on a "TEFLON"-coated drum and collected on a take-up roll operating at 30 feet/min (914 cm/minute) which resulted in the fabrics having a basis weight of 1.0 oz./square yard (34 gm/square meter).

Step 3. Repellency Testing

The oil repellent properties of the melt blown webs were measured using an oil drop test and are expressed in terms of an oil repellency rating (ORT). According to this test method, drops of standard test liquids, consisting of a selected series of hydrocarbons with varying surface tensions, were placed on the substrate and observed for wetting. The oil repellency rating is the highest numbered test liquid which will not wet the surface of the substrate within a period of 30 seconds. The standard test liquids and the corresponding ORT are given in Table 1.

TABLE 1

| ORT Ratings | |
|---|---|
| ORT | Test Liquid Composition |
| 1 | "NUJOL" |
| 2 | 65/35 "NUJOL"/n-hexadecane* |
| 3 | n-hexadecane |
| 4 | n-tetradecane |
| 5 | n-dodecane |
| 6 | n-decane |
| 7 | n-octane |
| 8 | n-heptane |

*mixture by volume at 70° F. (21° C.)

"NUJOL" is a trademark of Plough, Inc. for a mineral oil having a Saybolt viscosity of 360/390 at 100° F. (38° C.) and a specific gravity of 0.880/0.900 at 60° F. (15° C.).

The water repellent properties of the melt blown webs were measured using an isopropyl alcohol/water test and are expressed in terms of percent isopropyl alcohol. Webs that resist penetration of a 100 isopropyl alcohol/0% water solution (lowest surface tension fluid) after 1-2 minutes were given the highest rating of 100. Webs that were only resistant to a 100% water/0% isopropyl alcohol solution after 1-2 minutes were given the lowest rating of 0. Intermediate ratings of 20 to 90 in increments of 10 corresponded to solutions of 20% isopropyl alcohol/80% water to solutions of 90% isopropyl alcohol/10% water as shown in Table 2. The isopropyl alcohol repellency rating for a given fabric corresponded to the lowest surface tension fluid (greatest % isopropyl alcohol/water solution) that did not wet the fabric after 1-2 minutes.

TABLE 2

| IPA Ratings | |
|---|---|
| RATING | % Isopropyl alcohol/% water (vol/vol) |
| 100 | 100/0 |
| 90 | 90/10 |
| 80 | 80/20 |
| 70 | 70/30 |
| 60 | 60/40 |
| 50 | 50/50 |
| 40 | 40/60 |
| 30 | 30/70 |
| 20 | 20/80 |
| 10 | 10/90 |

Tables 3, 4, 5 and 6 summarize the oil repellency and isopropyl alcohol repellency data for the polypropylene melt blown webs containing Examples 1–26. Comparative Example A is "ZONYL" FTS. Also included in the tables is a polypropylene control sample noted as PP control. ORT is the oil repellency test rating. % IPA is the percent isopropylalcohol.

TABLE 3

ORT/Alcohol Repellency of Polypropylene Melt Blown Webs Containing Fluorochemicals of Formula A

| | | ORT/% IPA RATINGS | | | |
|---|---|---|---|---|---|
| | µg/g | INITIAL | | HEATED 220° F.*/10 min | |
| Example | Fluorine | ORT | % IPA | ORT | % IPA |
| 1 | 2660 | 0 | 30 | 4 | 100 |
| 2 | 2940 | 0 | 30 | 1 | 90 |
| 3 | 2810 | 0 | 30 | 1 | 80 |
| 4 | 3015 | 0 | 30 | 1 | 90 |
| 5 | 3060 | 0 | 30 | 1 | 90 |
| 6 | 2975 | 0 | 30 | 1 | 90 |
| 7 | 3015 | 0 | 30 | 0 | 90 |
| 8 | 2260 | 0 | 30 | 5 | 100 |
| 9 | 2800 | 0 | 30 | 0 | 80 |
| 10 | 2650 | 0 | 30 | 5 | 90 |
| 11 | 3390 | 0 | 30 | 1 | 40 |
| 12 | 2280 | 0 | 40 | 4 | 90 |
| 13 | 2890 | 0 | 30 | 3 | 100 |
| Compar. Ex. A | 2600 | 0 | 50 | 0 | 40 (1 min) |
| PP Control | 40 | 0 | 20 | 0 | 20 |

*104° C.

TABLE 4

ORT/Alcohol Repellency of Polypropylene Melt Blown Webs Containing Fluorochemicals of Formula B

| | | ORT/% IPA RATINGS | | | |
|---|---|---|---|---|---|
| | µg/g | INITIAL | | HEATED 140° F.*/22 hrs | |
| Example | Fluorine | ORT | % IPA | ORT | % IPA |
| 14 | 3190 | 1 | 80 | 0 | 70–80 |
| 15 | 3380 | 1 | 90 | 2 | 90 |
| Compar. Ex. A | 3840 | 0 | 60–70 | 0 | 60 |
| PP Control | 40 | 0 | 20 | 0 | 20 |

*60° C.

TABLE 5

ORT/Alcohol Repellency of Polypropylene Melt Blown Webs Containing Fluorochemicals of Formula C (Examples 16–19) and formula D (Examples 20–21).

| | | ORT/% IPA RATINGS | | | |
|---|---|---|---|---|---|
| | µg/g | INITIAL | | HEATED 140° F.*/22 hrs | |
| Example | Fluorine | ORT | % IPA | ORT | % IPA |
| 16 | 2650 | 0 | 30 | 0 | 80 |
| 17 | 2750 | 0 | 30 | 0 | 80 |
| 18 | 2880 | 0 | 30 | 0 | 90 |
| 19 | 2930 | 0 | 30 | 1 | 90 |
| 20 | 3050 | 0 | 30 | 1 | 90 |
| 21 | 3050 | 0 | 30 | 0 | 90 |
| Compar. Ex. A | 2690 | 0 | 50 | 0 | 40 (1 min) |
| PP Control | 40 | 0 | 20 | 0 | 20 |

*60° C.

TABLE 6

ORT/Alcohol Repellency of Polypropylene Melt Blown Webs Containing Fluorochemicals of Formula E

| | | ORT/% IPA RATINGS | | | | | |
|---|---|---|---|---|---|---|---|
| | µg/g | AS MADE | | 2 WEEKS | | HEATED 140 F.*/22 hrs | |
| Example | Fluorine | ORT | % IPA | ORT | % IPA | ORT | % IPA |
| 22 | 2480 | 0 | 30 | 0 | 30–40 | 0 | 40–50 |
| 23 | 2760 | 0 | 40–50 | 0 | 80 | 0 | 60 |
| 24 | 2990 | 0 | 40 | 1 | 80 | 0 | 50 |
| 24 | 3370 | — | 80 | — | 70 | — | 70** |
| 25 | 1930 | 0 | 40 | 0 | 40–50 | 0 | 50 |
| 25 | 1920 | — | 60 | — | 80 | — | 60** |
| 26 | 3450 | 0 | 50 | 1 | 90 | 2 | 100 |
| Compar. Ex.A | 2600 | 0 | 50 | 0 | 40 (1 min) | | |
| PP Control | 40 | 0 | 20 | 0 | 20 | | |

*60° C.
**Heated at 220° F. (104° C.) for 1 minute.
"—" indictes no data available

What is claimed is:

1. A composition comprising at least one thermoplastic polymer selected from the group consisting of polyolefin, polyester, polyamide and polyacrylate, and at least one compound selected from the group consisting of 1) a compound of formula A

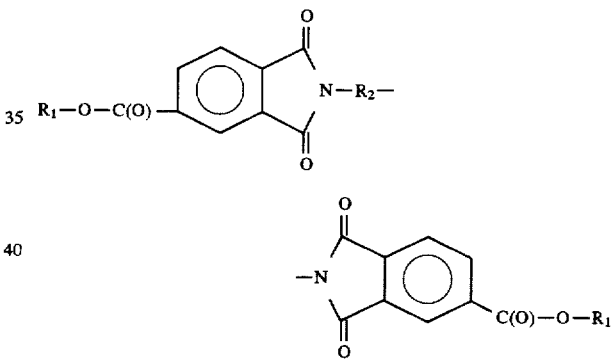

wherein $R_1$ is $F(CF_2)_x$—$(CH_2)_m$ or $F(CF_2)_xSO_2N(R_5)(CH_2)_p$ wherein x is from about 4 to about 20, m is from about 2 to about 6, p is from 1 to about 12, and $R_5$ is an alkyl radical of from 1 to about 4 carbons and $R_2$ is a linear, branched, or cyclic alkylene or poly (oxyalkylene) hydrocarbon group having from about 2 to about 15 carbons;

2) a compound of formula B

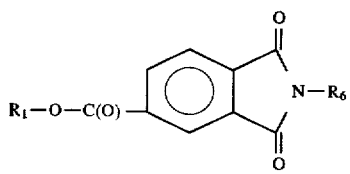

wherein $R_1$ is as defined above for formula A, and $R_6$ is a linear or branched alkyl having from about 4 to about 20 carbons;

3) a compound of formula C

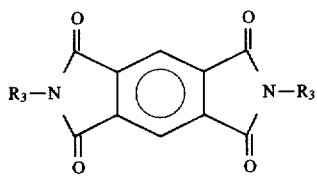

wherein

R₃ is selected from the group consisting of $F(CF_2)_x$—$(CH_2)_m$. $F(CF_2)_x$—$(CH_2)_m$—$OC(O)$—$(CH_2)_n$. and $F(CF_2)_xSO_2N(R_5)(CH_2)_pOC(O)(CH_2)_n$ wherein x is from about 4 to about 20, m is from about 2 to about 6, and n is about 2 to about 12, p is from 1 to about 12, and R₅ is an alkyl radical of from 1 to about 4 carbons;

4) a compound of formula D

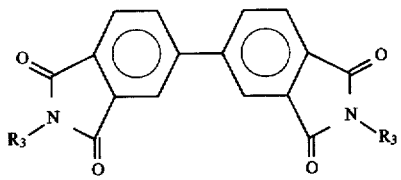

wherein

R₃ is as defined above for formula C; and 5) a compound of formula E

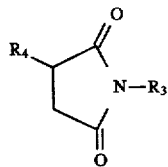

wherein

R₃ is as defined above for formula C; and

R₄ is an alkyl or alkenyl group of from about 4 to about 20 carbons, and 6) mixtures of compounds A through E.

2. The composition of claim 1 wherein the polymer is selected from the group consisting of polyolefin, mixture of polyolefins, polyolefin copolymer, mixture of polyolefin copolymers, and mixture of at least one polyolefin and at least one polyolefin copolymer.

3. The composition of claim 2 wherein the polymer has a polymer or copolymer unit which is ethylene, propylene, butylene, or mixtures thereof.

4. A film comprising a film forming thermoplastic polymer having dispersed therein from about 0.1% to about 5% by weight of the polymer of an additive which improves the repellency of the film to low surface tension fluids, said additive being selected from the group consisting of 1) a compound of formula A

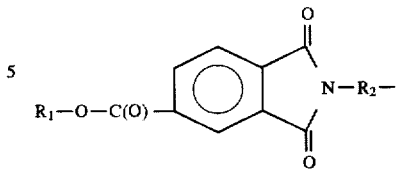

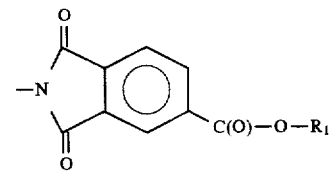

wherein

R₁ is $F(CF_2)_x$—$(CH_2)_m$ or $F(CF_2)_xSO_2N(R_5)(CH_2)_p$ wherein x is from about 4 to about 20, m is from about 2 to about 6, p is from 1 to about 12, and R₅ is an alkyl radical of from 1 to about 4 carbons and R2 is a linear, branched, or cyclic alkylene or poly (oxyalkylene) hydrocarbon group having from about 2 to about 15 carbons;

2) a compound of formula B

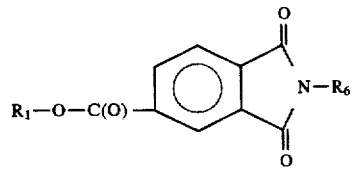

wherein

R₁ is as defined above for formula A, and

R₆ is a linear or branched alkyl having from about 4 to about 20 carbons;

3) a compound of formula C

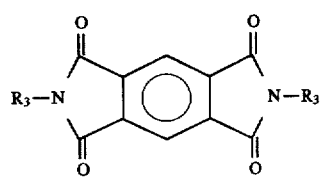

wherein

R₃ is selected from the group consisting of $F(CF_2)_x$—$(CH_2)_m$. $F(CF_2)_x$—$(CH_2)_m$—$OC(O)$—$(CH_2)_n$. and $F(CF_2)_xSO_2N(R_5)(CH_2)_pOC(O)(CH_2)_n$ wherein x is from about 4 to about 20, m is from about 2 to about 6, and n is about 2 to about 12, p is from 1 to about 12, and R₅ is an alkyl radical of from 1 to about 4 carbons;

4) a compound of formula D

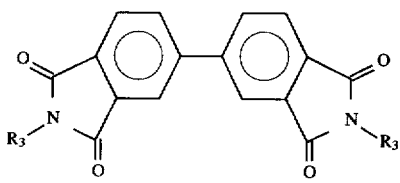

wherein

R₃ is as defined above for formula C; and 5) a compound of formula E

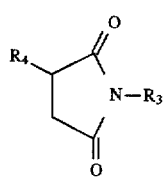

wherein

R₃ is as defined above for formula C; and

R₄ is an alkyl or alkenyl group of from about 4 to about 20 carbons, and 6) mixtures of compounds A through E.

5. A film of claim 4 wherein said film has a fluorine content of from about 200 µg/g to about 25,000 µg/g.

6. A molded article comprising a thermoplastic polymer having dispersed therein from about 0.1% to about 5% by weight of the polymer of an additive which improves the repellency of the article to low surface tension fluids, said additive being selected from the group consisting of 1) a compound of formula A

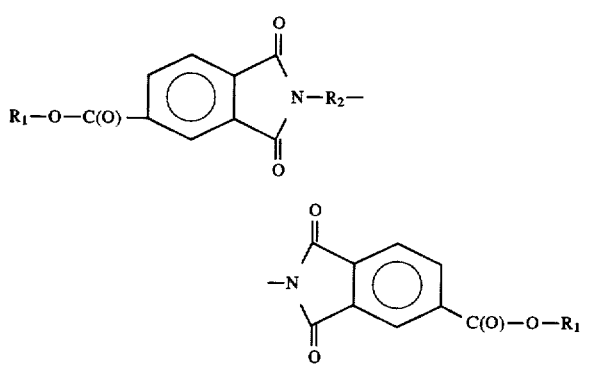

wherein

R₁ is F(CF₂)ₓ—(CH₂)ₘ or F(CF₂)ₓSO₂N(R₅)(CH₂)ₚ wherein x is from about 4 to about 20, m is from about 2 to about 6, p is from 1 to about 12, and R₅ is an alkyl radical of from 1 to about 4 carbons and R2 is a linear, branched, or cyclic alkylene or poly(oxyalkylene) hydrocarbon group having from about 2 to about 15 carbons;

2) a compound of formula B

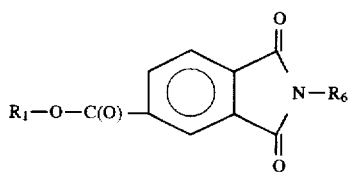

wherein

R₁ is as defined above for formula A, and

R₆ is a linear or branched alkyl having from about 4 to about 20 carbons;

3) a compound of formula C

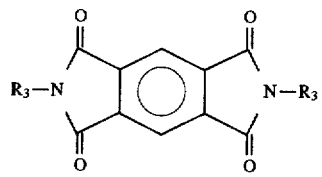

wherein

R₃ is selected from the group consisting of F(CF₂)ₓ—(CH₂)ₘ, F(CF₂)ₓ—(CH₂)ₘ—OC(O)—(CH₂)ₙ, and F(CF₂)ₓSO₂N(R₅)(CH₂)ₚOC(O)(CH₂)ₙ
wherein x is from about 4 to about 20, m is from about 2 to about 6, and n is about 2 to about 12, p is from 1 to about 12, and R₅ is an alkyl radical of from 1 to about 4 carbons;

4) a compound of formula D

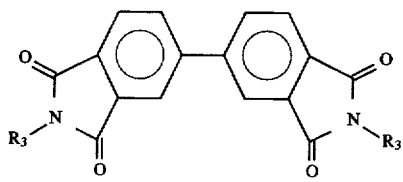

wherein

R₃ is as defined above for formula C; and 5) a compound of formula E

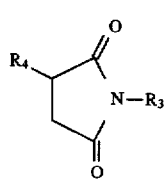

wherein

R₃ is as defined above for formula C; and

R₄ is an alkyl or alkenyl group of from about 4 to about 20 carbons, and 6) mixtures of compounds A through E.

7. A molded article of claim 6 wherein said article has a fluorine content of from about 200 µg/g to about 25,000 µg/g.

* * * * *